*(12)* United States Patent
Powell et al.

(10) Patent No.: US 9,065,197 B2
(45) Date of Patent: Jun. 23, 2015

(54) PROTECTION STRUCTURE FOR IMPLANTABLE CONNECTOR AND APPARATUS FOR MANIPULATING SAME

(71) Applicant: Cochlear Limited, Macquarie University, NSW (AU)

(72) Inventors: Anthony Powell, Bondi Junction (AU); C. Roger Leigh, East Ryde (AU); James Dalton, Beecroft (AU)

(73) Assignee: COCHLEAR LIMITED, Macquarie University, NSW (AU)

( * ) Notice: Subject to any disclaimer, the term of this patent is extended or adjusted under 35 U.S.C. 154(b) by 60 days.

(21) Appl. No.: 13/851,358

(22) Filed: Mar. 27, 2013

(65) Prior Publication Data

US 2014/0273576 A1    Sep. 18, 2014

Related U.S. Application Data

(60) Provisional application No. 61/789,546, filed on Mar. 15, 2013.

(51) Int. Cl.
*H01R 13/52* (2006.01)
*H01R 43/00* (2006.01)
*A61N 1/375* (2006.01)

(52) U.S. Cl.
CPC .......... *H01R 13/5219* (2013.01); *H01R 43/005* (2013.01); *Y10T 29/53209* (2015.01); *A61N 1/375* (2013.01); *H01R 2201/12* (2013.01)

(58) Field of Classification Search
CPC .. H01R 13/5219; H01R 43/005; H01R 13/52; H01R 43/00; H01R 2201/12; A61N 1/375; Y10T 29/53209
USPC ............. 439/271, 289, 909, 272, 283; 29/747
See application file for complete search history.

(56) References Cited

U.S. PATENT DOCUMENTS

| 4,971,057 A | 11/1990 | Theres |
| 7,844,329 B2 | 11/2010 | Chambers |
| 8,267,708 B1 * | 9/2012 | Sochor .......................... 439/289 |

FOREIGN PATENT DOCUMENTS

WO     2004/097993     11/2004

\* cited by examiner

*Primary Examiner* — Javaid Nasri

(57) ABSTRACT

An implantable connector includes: first and second detachable mating parts configured to be implantable in living tissue, to terminate first and second segments of a cable, and have first and second interfacing surfaces, respectively; and a protection structure configured to protect against contaminant intrusion between the first and second interfacing surfaces. And a device for decoupling and re-coupling the detachable mating parts in an environmentally controllable volume is provided.

23 Claims, 13 Drawing Sheets

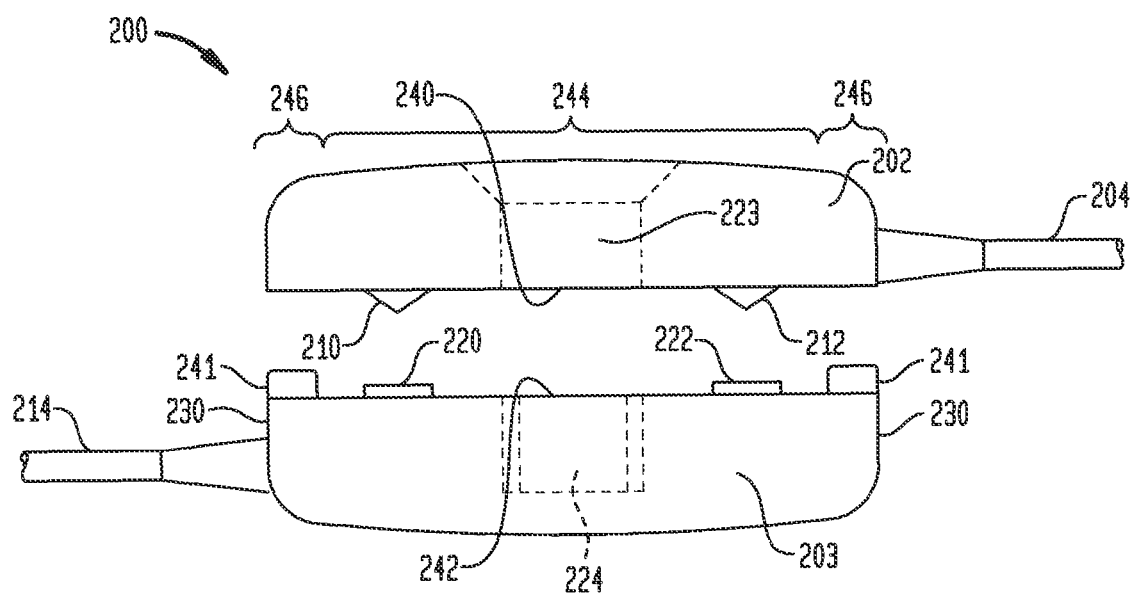

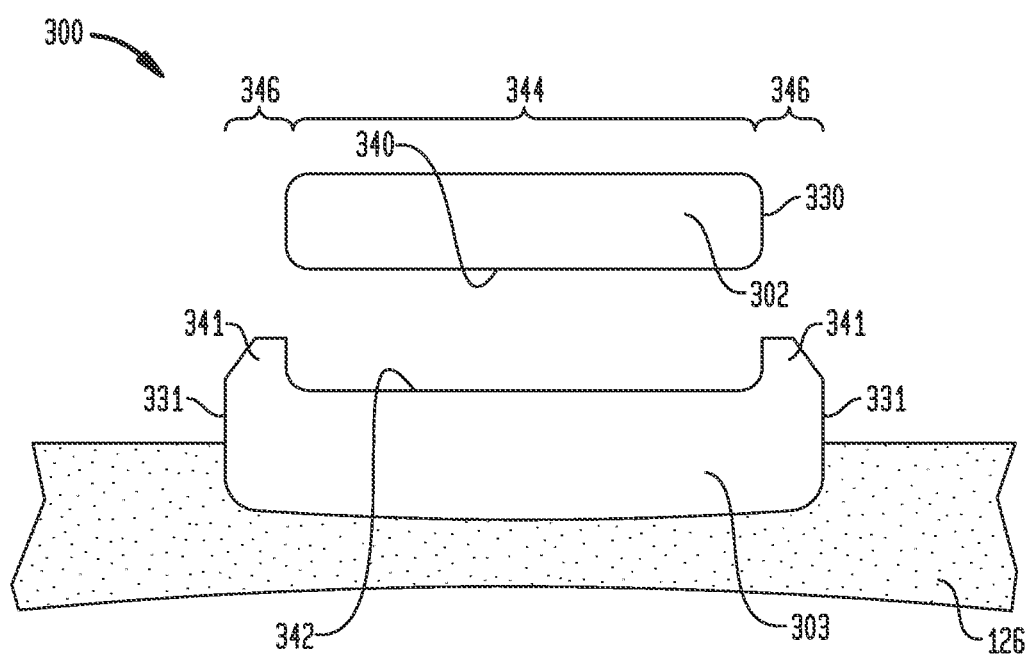

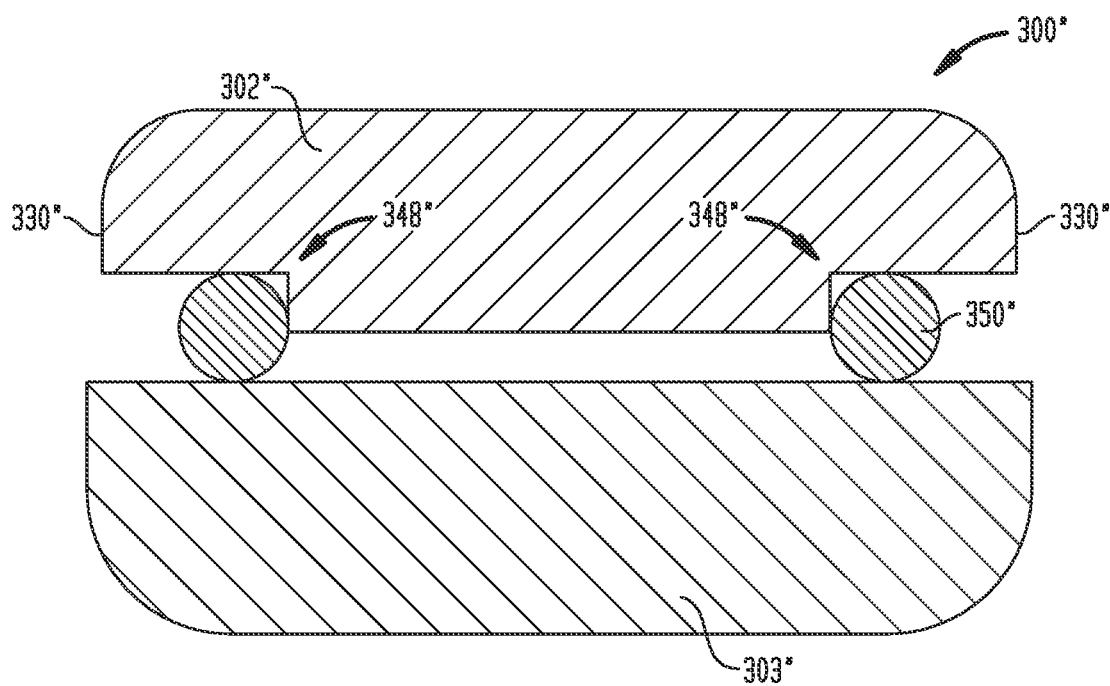

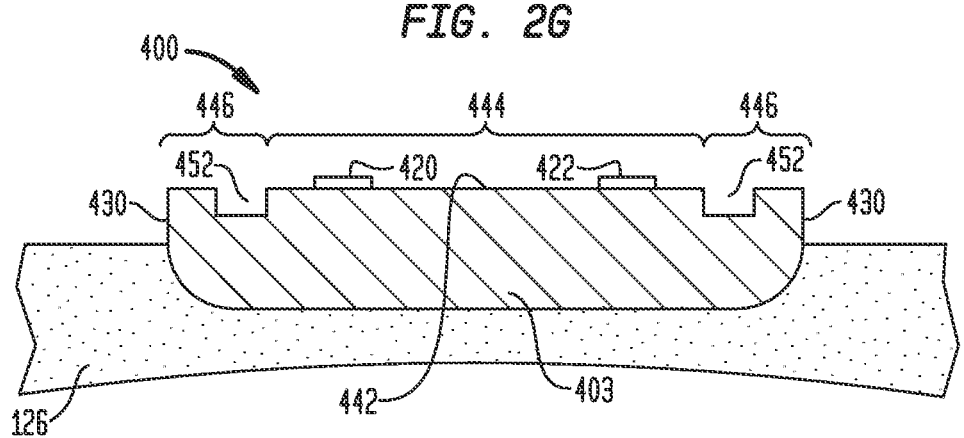
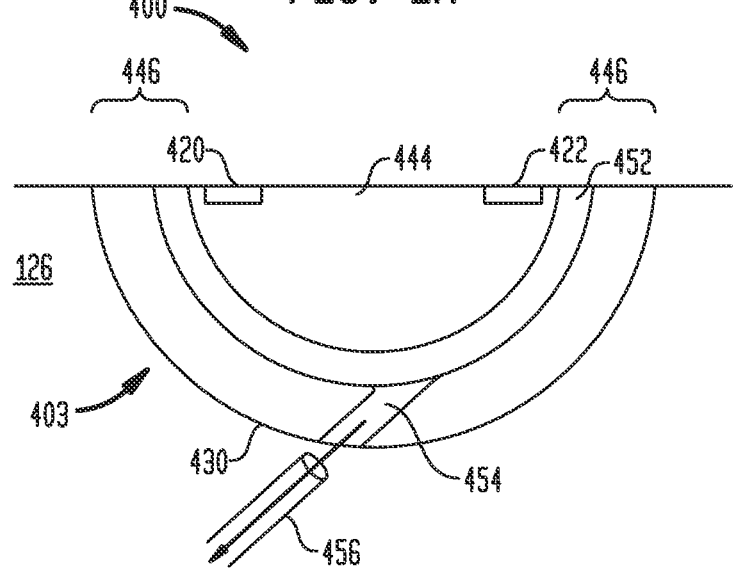

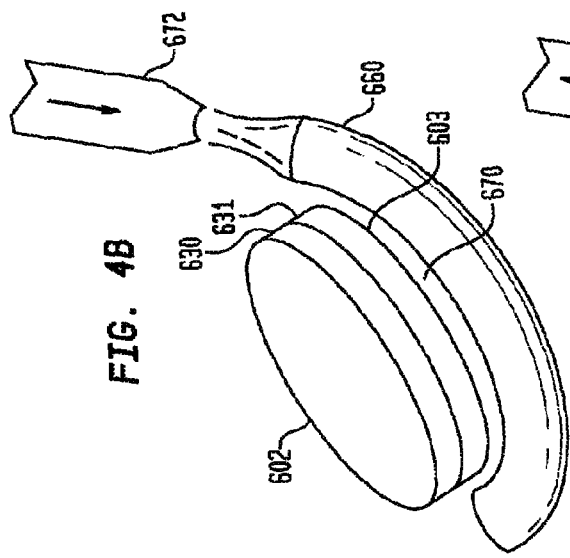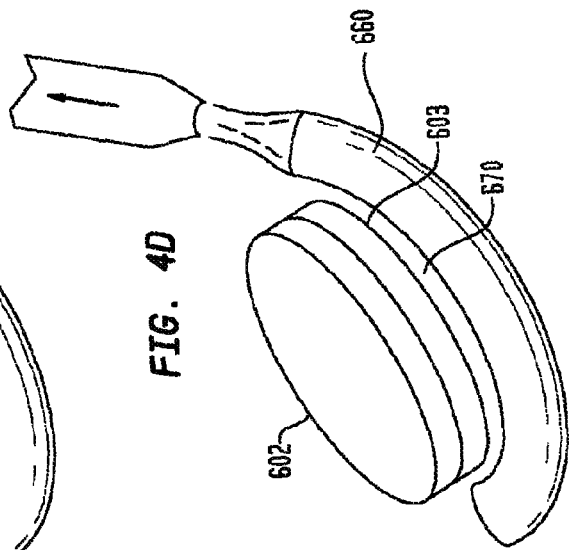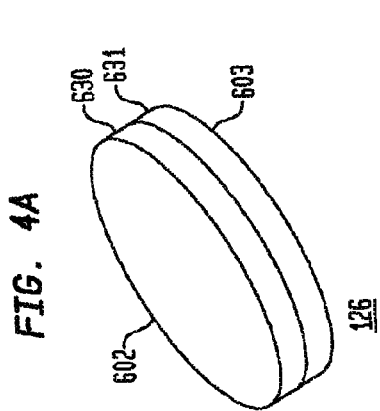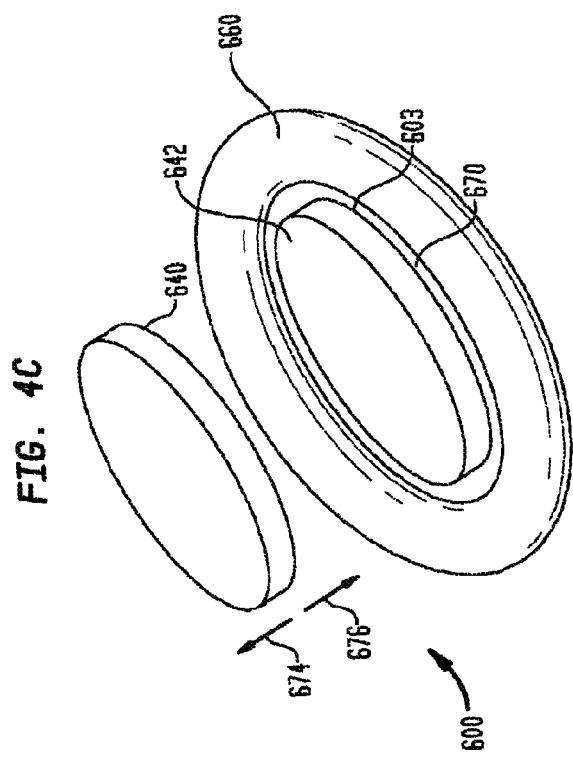

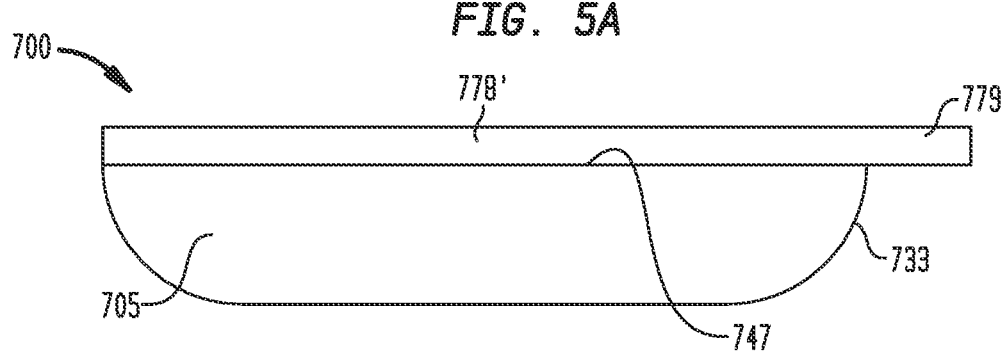
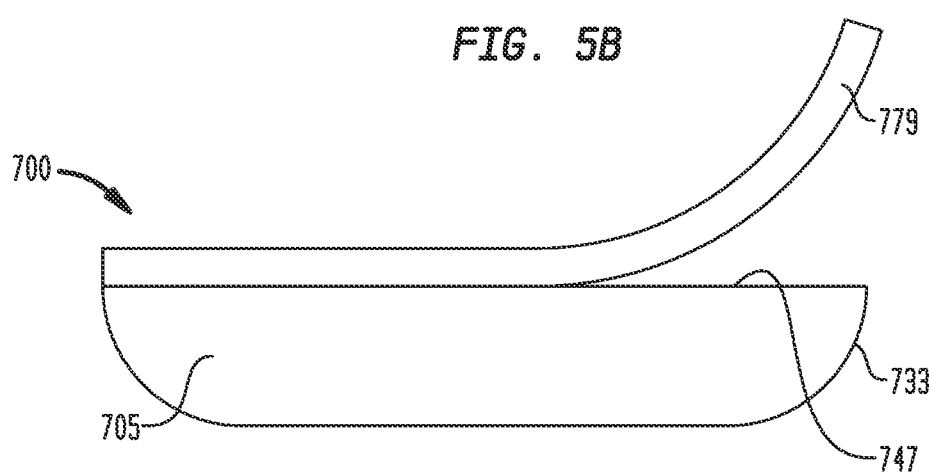

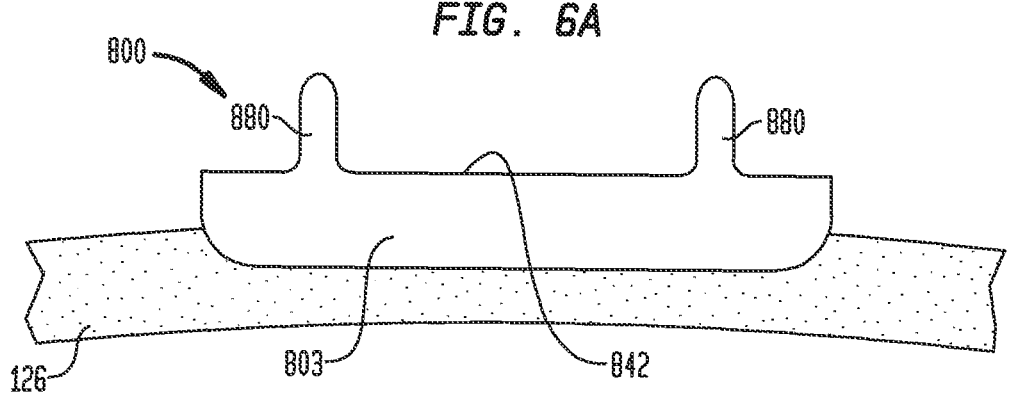
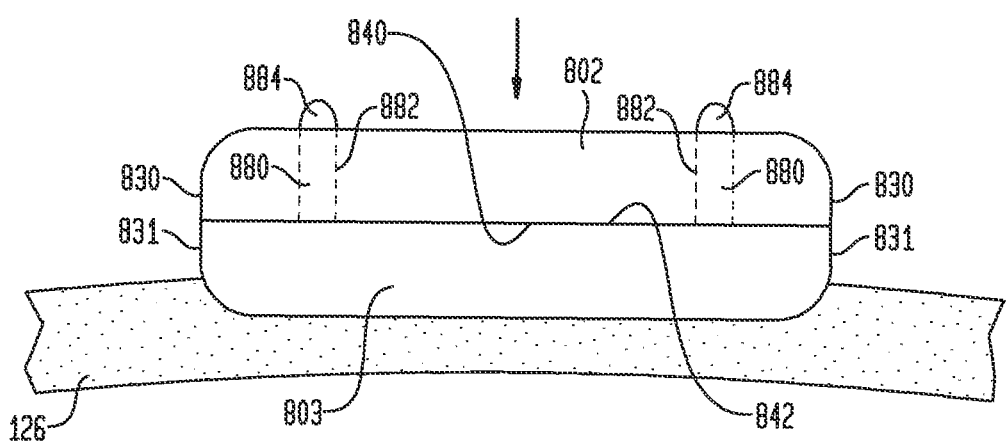
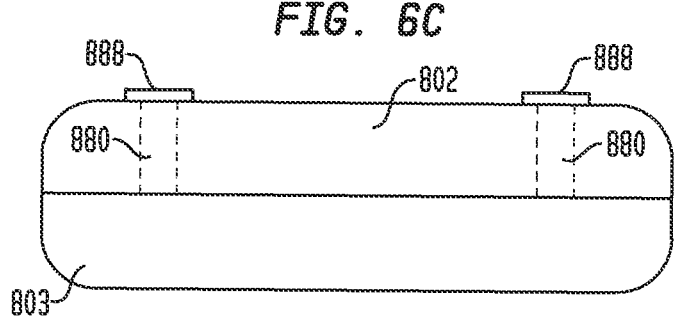

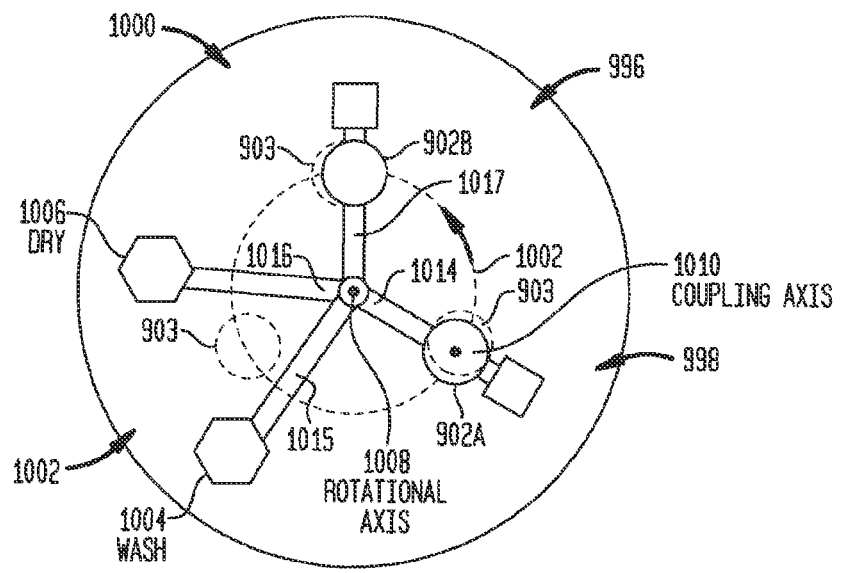
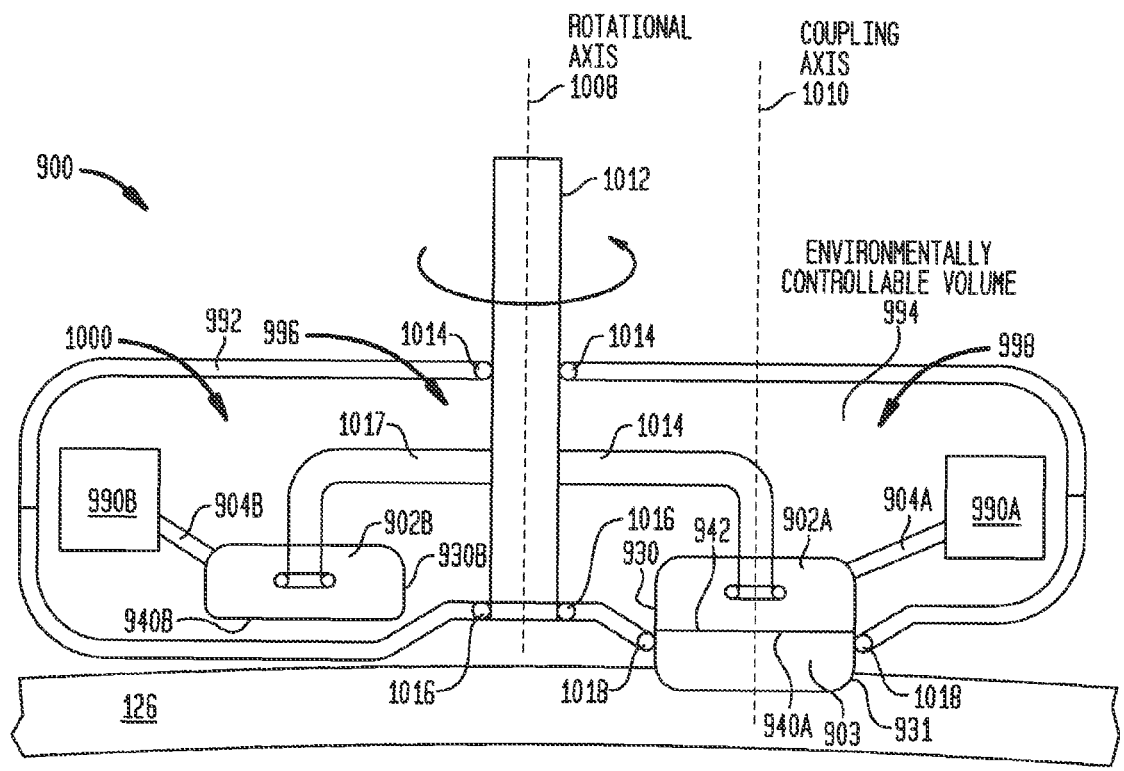

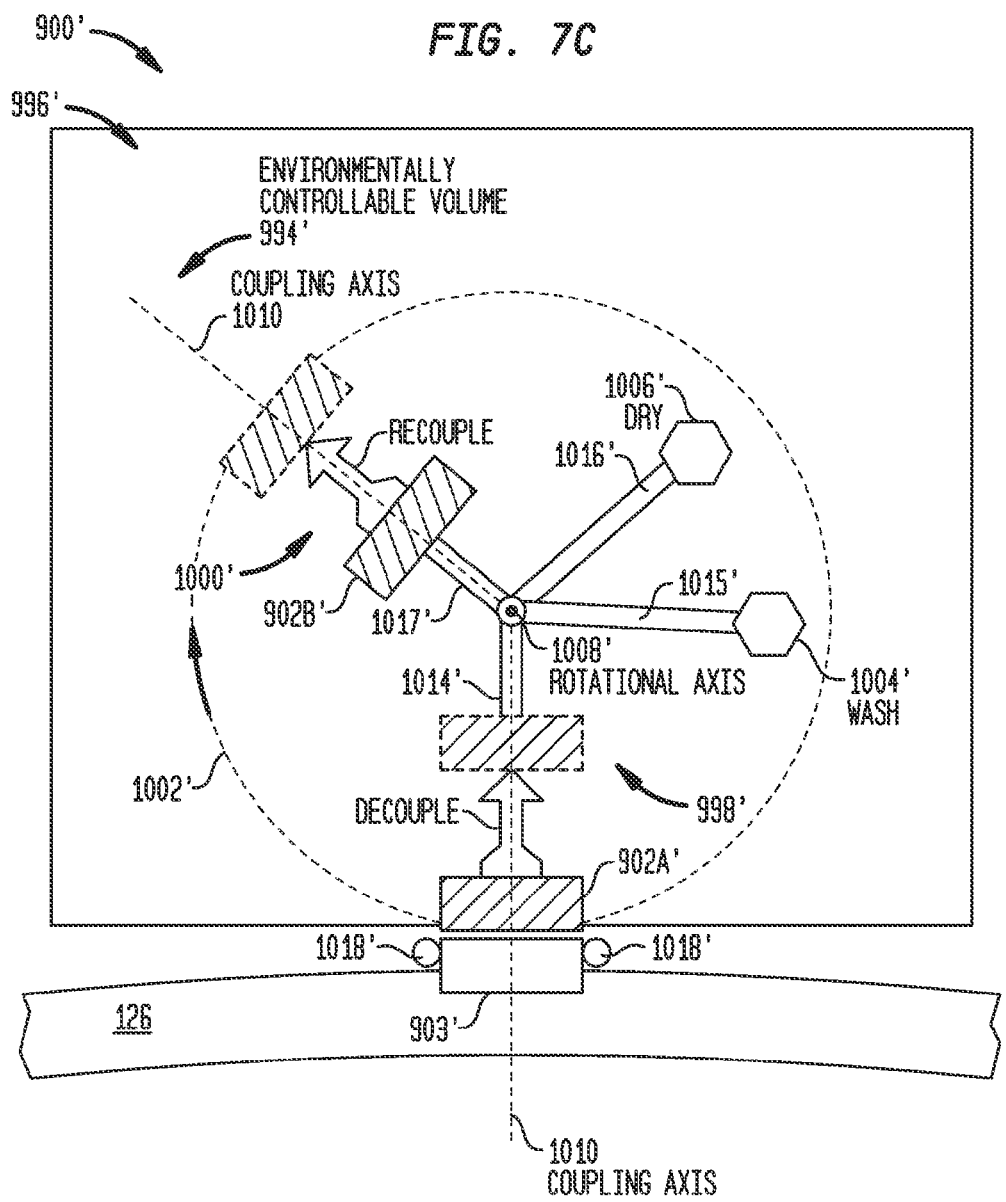

PROTECTION STRUCTURE FOR IMPLANTABLE CONNECTOR AND APPARATUS FOR MANIPULATING SAME

CROSS-REFERENCE TO RELATED APPLICATIONS

This application claims the benefit of U.S. Provisional Patent Application No. 61/789,546, filed Mar. 15, 2013. The content of this application is hereby incorporated by reference herein.

BACKGROUND

1. Field of the Disclosure

The present technology relates generally to detachable mating parts of an implantable connector that terminate segments of a cable, and to a device for manipulating detachment and/or re-attachment of such mating parts.

2. Related Art

Implantable medical devices often have more than one implantable component. Such components are typically connected by one or more cables through which the components communicate, transfer data and/or transfer power. Such a cable typically comprises one or more electrical conductors and is configured with a segment that terminates with a mating part of an implantable connector. The detachable mating parts of the connector facilitate replacement of device components when such components fail, are consumed, or are in need of being updated. For example, an implantable connector on a device requiring an implanted battery facilitates replacement of the battery.

For some implantable connectors, it is important to exclude body fluids from the mating surfaces of the mating parts. Body fluids are ionic, which can cause current leakage between the conductors in the short term. In the long term, ionic body fluids may precipitate dendritic growth between the mating surfaces, which can contribute to device failure.

On the occasion of decoupling and re-coupling the detachable mating parts of such a connector in a surgical environment where body fluids present exposure of the mating surfaces of the mating parts to the bodily fluids is a risk.

SUMMARY

In one aspect of the present technology an implantable connector is provided. The implantable connector includes: first and second detachable mating parts and a protection structure. The first and second mating parts are configured: to be implantable in living tissue; to terminate first and second segments of a cable; and have first and second interfacing surfaces, respectively. The protection structure is configured to protect against contaminant intrusion between the first and second interfacing surfaces.

In another aspect of the present technology, a system for protecting an implantable connector is provided. The connector to be protected has first and second detachable mating parts configured to be implantable in living tissue and terminate first and second segments of a cable, each mating part having an interfacing surface bounded by one or more sidewalls. Such a system includes: a protection structure configured to enclose the one or more sidewalls of at least one of the first and second mating parts.

In yet another aspect of the present technology, a system for protecting a mating part of an implantable connector is provided. Such a system includes: a first detachable mating part; and a protection structure. The mating part is configured to: be implantable in living tissue; terminate a segment of a cable; have an interfacing surface; and engage with a corresponding second detachable, implantable mating part. The protection structure is configured to protect the interfacing surface against contamination.

In yet another aspect of the present technology, an implantable connector is provided. Such a connector includes first and second detachable mating parts. Each mating part is configured: to be implantable in living tissue; to terminate first and second segments of a cable; and to have first and second interfacing surfaces, respectively. The first mating part includes: at least one alignment projection extending substantially perpendicularly from the first interfacing surface. The second mating part includes at least one alignment hole corresponding to the at least one alignment projection, respectively. Each alignment hole is complementarily shaped to receive the corresponding alignment projection.

In yet another aspect of the present technology, there is provided a machine for manipulating first and second detachable mating parts of an implantable connector that terminate first and second segments of a cable. Such a machine includes: an enclosure configured to releasably enclose at least the second mating part and a portion of the first mating part in an environmentally controllable volume; and a coupling device configured to at least one of decouple and re-couple the first and second mating parts, respectively, while the second mating part and the portion of the first mating part are disposed in the environmentally controllable volume.

BRIEF DESCRIPTION OF THE DRAWINGS

Embodiments of the present technology are described below with reference to the attached drawings, in which:

FIG. 2A is an exploded side view of an implantable connector in which some embodiments of the present technology may be implemented;

FIG. 2B is an exploded cross-section of another implantable connector in which some embodiments of the present technology may be implemented;

FIG. 2F is a cross-section of another implantable connector in which some embodiments of the present technology may be implemented;

FIG. 2G is a cross-section, and FIG. 2H is a top view of one-half, of a mating part of another implantable connector in which some embodiments of the present technology may be implemented;

FIG. 3A is a three-quarter perspective view, and FIGS. 3B-3C are cross-sections, of a system, in which some embodiments of the present technology may be implemented, for protecting an implantable connector against contaminant intrusion between mating parts of the connector;

FIG. 3D is a cross-section of another system, in which some embodiments of the present technology may be implemented, for protecting an implantable connector against contaminant intrusion between mating parts of the connector;

FIGS. 4A-4D are cross-sections that together illustrate another system in which some embodiments of the present technology may be implemented, for protecting an implantable connector against contaminant intrusion between mating parts of the connector;

FIGS. 5A-5B are cross-sections of another system in which some embodiments of the present technology may be implemented, the system being for protecting a mating part of an implantable connector against contaminant intrusion;

FIGS. 6A-6C are cross-sections of another connector in which some embodiments of the present technology may be implemented.

FIG. 7A is a top view, and FIG. 7B is a cross-section, of a machine in which some embodiments of the present technology may be implemented, the machine being for manipulating mating parts of an implantable connector; and FIG. 7C is a cross-section of another machine in which some embodiments of the present technology may be implemented, the machine being for manipulating mating parts of an implantable connector.

DETAILED DESCRIPTION

Figure 1A:
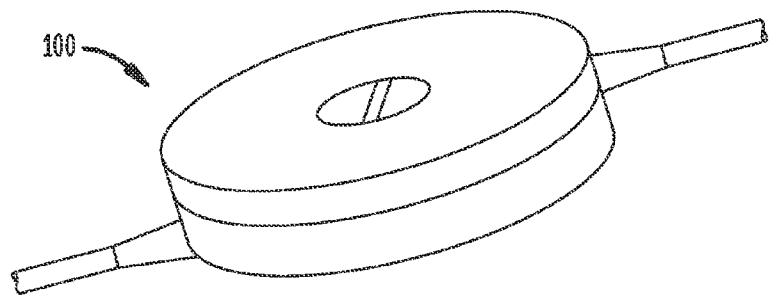
FIG. 1A is a three-quarter perspective view.

Aspects of the present technology relate to an implantable connector including: first and second detachable mating parts; and a protection structure configured to protect against contaminant intrusion between the first and second interfacing surfaces of the first and second mating parts. Without the protection structure, the interfacing surfaces are otherwise at risk of contamination, e.g., on the occasion of decoupling and/or re-coupling the detachable mating parts in a surgical environment where body fluids present, e.g., in a context of replacing an expired battery, exposure of the mating surfaces of the mating parts to the bodily fluids is a risk.

Another aspect of the present technology relates to a system for protecting an implantable connector having first and second detachable mating parts configured to be implantable in living tissue and terminate first and second segments of a cable. Each mating part has an interfacing surface bounded by one or more sidewalls. The system includes a protection structure configured to enclose the one or more sidewalls of at least one of the first and second mating parts. For example, the protection structure can include a hollow cylinder configured to abuttingly enclose at least the one or more sidewalls of the second mating part. As another example, the protection structure can be a coffer dam disposed on the tissue and configured to enclose at least the one or more sidewalls of the second mating part.

Another aspect of the present technology relates to another protection structure configured to protect the interfacing surface against contamination, e.g., by taking the form of a removable layer of material disposed in contact with the interfacing surface so as to seal the same from the ambient environment. Such a removable layer protects the interfacing surface until the mating part is ready for coupling to a counterpart mating part, at which time the person intending to couple the mating parts, e.g., a surgeon, can remove the removable layer of material.

Another aspect of the present technology relates to an implantable connector including first and second detachable mating parts. The first mating part includes at least one alignment projection extending substantially perpendicularly to the first interfacing surface. The second mating part includes at least one alignment hole corresponding to the at least one alignment projection, respectively. Each alignment hole is complementarily shaped to receive the corresponding alignment projection. Each alignment projection, e.g., can include: a first portion extending from the first interfacing surface into the recess; and a second portion standing proud of the corresponding second surface of the second mating part. The proud-standing portion of each alignment projection, e.g., can be configured as a flange that resists a tendency (if any) for the mating parts to decouple.

Another aspect of the present technology relates to a machine for manipulating first and second detachable mating parts of an implantable connector that terminate first and second segments of a cable. Such a machine includes: an enclosure configured to releasably enclose at least the second mating part and a portion of the first mating part in an environmentally controllable volume; and a coupling device configured to at least one of decouple and re-couple the first and second mating parts, respectively, while the second mating part and the portion of the first mating part are disposed in the environmentally controllable volume.

The coupling device includes, e.g., a decoupling apparatus and a re-coupling apparatus. During the operation of the machine, the first mating part is stationary relative to instances of the second mating part. The decoupling apparatus is configured to: decouple the first mating part and a first instance of the second mating part; and move the first instance of the second mating part along an arcuate path away from the first mating part. The re-coupling apparatus is configured to: move a second instance of the second mating part along the arcuate path towards the first mating part; and re-couple the first mating part to the second instance of the second mating part. There is a rotational axis about which the motion along the arcuate path occurs. And there is a coupling axis associated with the motions of decoupling and re-coupling. The coupling axis is either substantially orthogonal or substantially parallel to the rotational axis.

Figure 1B:
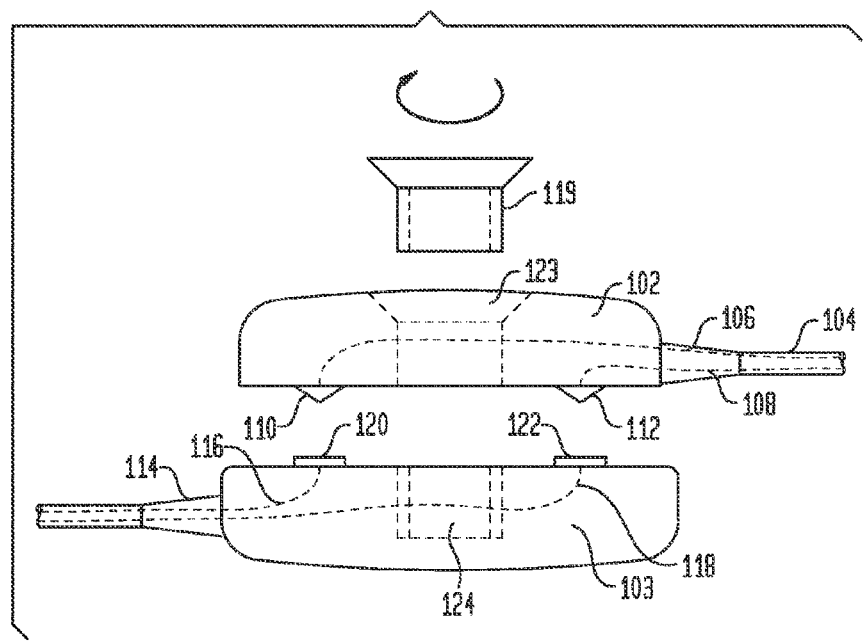
FIGS. 1B and 1D are cross-sections (FIG. 1D being relatively simplified), of an implantable connector.

FIG. 1A is a three-quarter perspective view of an implantable connector 100. FIG. 1B is an exploded side view of connector 100. And FIG. 1C is an exploded three-quarter perspective view of implantable connector 100.

Implantable connector 100 is a button type of connector that includes: a first detachable mating part 102 and a second detachable mating part 103 corresponding thereto. Mating parts 102 and 103 terminate a first segment 104 and a second segment 114 of a cable. In FIGS. 1B-1C, the cable is illustrated as including first and second signal lines, the first signal line including segments 106 and 116, the second signal line including segments 108 and 118. Signal line segments 106 and 108 are connected to electrodes 110 and 112, respectively, and signal line segments 116 and 118 are connected to electrodes 120 and 122, respectively. It is noted that fewer and greater numbers of signal lines and corresponding electrodes are contemplated. On any given signal line, various signals are contemplated as being conducted, e.g., power, data, control, communication, etc., respectively. While electrodes 110 and 112 are illustrated as having triangular cross sections, and electrodes 120 and 122 are illustrated as having rectangular cross sections, other shapes are contemplated for the electrodes. While illustrated as being a button type, other types of connectors are contemplated for connector 100. The various components of connector 100 are formed of biocompatible materials, e.g., including one or more of Titanium, Silicone, Ceramic, Platinum, Platinum/Iridium, polyether ether ketone (PEEK), etc.

Connector 100 also includes, for example, a frictional engaging member 119, e.g., a screw, that can be inserted through a corresponding through-hole (e.g., unthreaded) 123 in mating part 102 and into a corresponding complementarily-shaped frictional engaging recess 124, e.g., a threaded hole, in mating part 103. When inserted through through-hole 123 into hole 124, screw 119 applies a force to mating part 102 that urges mating part 102 to abut mating part 103, i.e., urges mating part 102 to couple with mating part 103. More particularly, the force applied by screw 119 urges electrodes 110 and 112 to abut and thus to connect to electrodes 120 and 122, respectively. The force applied by screw 119 also resists a tendency of mating parts 102 and 103 to decouple. In addition, holes 123 and 124 are formed in alignment so that the insertion of screw 119 causes mating parts 102 and 103 to align, thereby facilitating good electrical connections between corresponding electrodes 110 and 120, and corresponding electrodes 112 and 122.

Figure 1D:
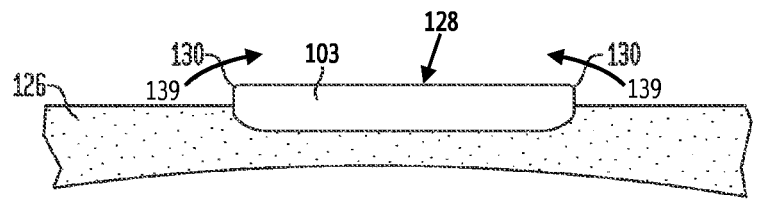
Figure 1C:
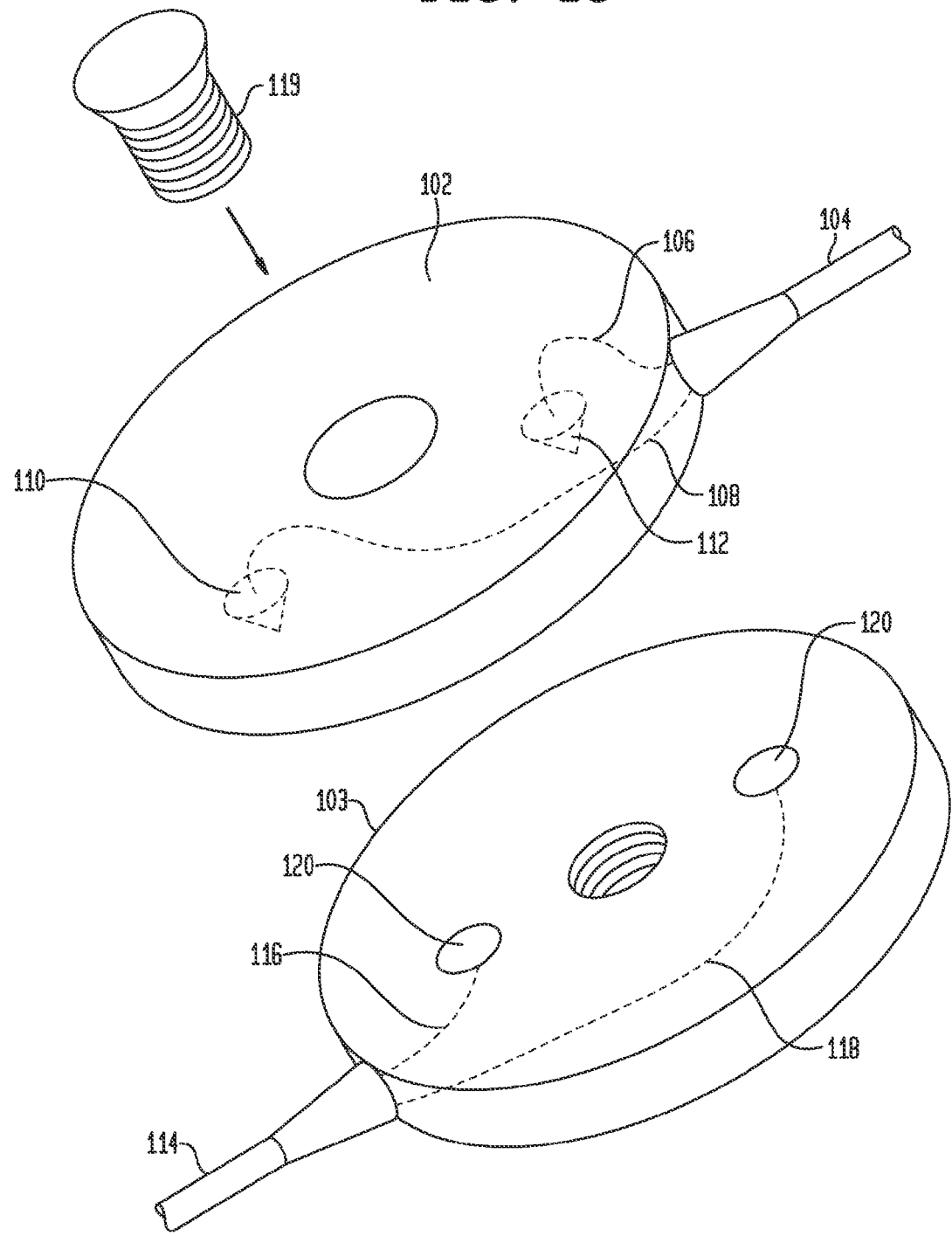
FIG. 1C is an exploded three-quarter perspective view.

FIG. 1D illustrates one of mating parts 102 and 103, e.g., 103, implanted in bone 126, e.g., in the midst of a surgical procedure, e.g., a procedure to replace an instance of mating part 102 ("replacee mating part 102") by another instance of mating part 102 ("replacer mating part 102") while mating part 103 remains in its implanted position. When replacee mating part 102 is decoupled from mating part 103, a surface 128 of mating part 103 on which the electrodes are located is placed at risk of contamination by body fluids that wash over sidewalls 130 of mating part 103. Mating parts 102 and 103 also can begin in a decoupled state before they are initially coupled (e.g., such as when mating part 103 is implanted albeit before being initially coupled with mating part 102), during which time surface 128 of mating part 103 is similarly at risk of contamination by body fluids that wash/seep/migrate over sidewalls 130 as shown by arrows 139.

FIG. 2A is an exploded side view of an implantable connector 200 in which some embodiments of the present technology may be implemented. Connector 200 is similar in many respects to connector 100 of FIGS. 1A-1C, as indicated by similar numbering.

Implantable connector 200, e.g., a button type of connector, includes: a first detachable mating part 202 and a second detachable mating part 203 corresponding thereto. Mating parts 202 and 203 terminate a first segment 204 and a second segment 214 of a cable, respectively. In FIG. 2A, the cable includes first and second signal lines (not illustrated). Segments (not illustrated) of the first signal line are connected to electrodes 210 and 212, respectively. Segments (not illustrated) of the second signal line are connected to electrodes 220 and 222, respectively. It is noted that fewer and greater numbers of signal lines and corresponding electrodes are contemplated. On any given signal line, various signals are contemplated as being conducted, e.g., power, data, control, communication, etc., respectively. While electrodes 210 and 212 are illustrated as having triangular cross sections, and electrodes 220 and 222 are illustrated as having rectangular cross sections, other shapes are contemplated for the electrodes. While illustrated as being a button type, other types of connectors are contemplated for connector 200. The various components of connector 200 are formed of biocompatible materials, e.g., including one or more of Titanium, Silicone, Ceramic, Platinum, Platinum/Iridium, polyether ether ketone (PEEK), etc.

Connector 200 also includes, for example, a frictional engaging member (not illustrated), e.g., a screw, that can be inserted through a corresponding through-hole (e.g., unthreaded) 223 in mating part 202 and into a corresponding complementarily-shaped frictional engaging recess 224, e.g., a threaded hole, in mating part 203. When inserted through through-hole 223 into hole 224, the screw applies a force to mating part 202 that urges mating part 202 to abut mating part 203, i.e., urges mating part 202 to couple with mating part 203. More particularly, the force applied by the screw urges electrodes 210 and 212 to abut and thus to connect to electrodes 220 and 222, respectively. The force applied by the screw also resists a tendency of mating parts 202 and 203 to decouple. In addition, holes 223 and 224 are formed in alignment so that the insertion of the screw causes mating parts 202 and 203 to align, thereby facilitating good electrical connections between corresponding electrodes 210 and 220, and corresponding electrodes 212 and 222.

Mating parts 202 and 203 of connector 200 have interfacing surfaces 240 and 242, respectively. Each of interfacing surfaces 240 and 242 is arranged with an inner area 244, e.g., a circular area, enclosed by an outer area 246, e.g., an annular outer area. Electrodes 210, 212, 220 and 222 are provided on inner areas 244, and corresponding electrodes 212 and 222.

In FIG. 2A, mating parts 202 and 203 are illustrated in a decoupled state. As noted, e.g., a decoupled state can arise in the context of a surgical procedure, e.g., a procedure to replace an instance of mating part 202 ("replacee mating part 202") by another instance of mating part 202 ("replacer mating part 202") while mating part 203 remains in its implanted position, e.g., implanted in bone, or mating parts 202 and 203 can begin in a decoupled state before they are initially coupled, etc. Assuming the replacement scenario for the purposes of discussion, when replacee mating part 202 is decoupled from mating part 203, interfacing surface 242 of mating part 203 on which electrodes 220 and 222 are located is placed at risk of contamination by body fluids that wash over sidewalls 230 of mating part 203.

To protect against such a risk, connector 200 further includes a protection structure 241, e.g., a wall, projecting from interfacing surface 242 and configured to protect interfacing surfaces 240 and 242 against contaminant intrusion. Wall 241 is formed on, e.g., outer area 246 of interfacing surface 242, and can align with sidewalls 230 or be located inward thereof. Wall 241 is configured to enclose inner areas 244 of interfacing surfaces 240 and 242. While mating parts 202 and 203 are decoupled, wall 241 protects inner area 244 of interfacing surface 242, and thus electrodes 220 and 222, from contamination by body fluids that otherwise might wash over sidewalls 230 of mating part 203. When mating part 202 is coupled to mating part 203, wall 241 is of sufficient height (equal to or greater than the combined heights of electrodes 210 and 220, and 212 and 222, respectively) so that wall 240 forms a seal between mating parts 202 and 203. Wall 241 can be formed of the same material as mating part 203. Alternatively, wall 241 can be formed of a relatively more resilient material, or a foam or viscous material, that deforms upon compression to enhance the seal made by wall 241 against outer surface 246 of interfacing surface 240. Alternatively, wall 241 can have a counterpart wall (not illustrated) formed on outer area 246 of interfacing surface 240 of mating part 202 in addition to (or instead of) wall 241. For example, wall 241 and counterpart wall can be aligned with each other similar to how the electrode pairs are aligned.

FIG. 2B is an exploded cross-section of another implantable connector 300 in which some embodiments of the present technology may be implemented. Connector 300 is similar in many respects to connector 200 of FIG. 2A, as indicated by similar numbering, and in some respects has been illustrated in less detail for the sake of brevity.

Mating parts 302 and 303 of connector 300 have interfacing surfaces 340 and 342, respectively. Each of interfacing surfaces 340 and 342 is arranged with an inner area 344, e.g., a circular area, and interfacing surface 342 is arranged with an outer area 346, e.g., an annular outer area, that encloses inner area 344 of interfacing surface 342. Corresponding electrode pairs (not illustrated) are provided on inner areas 344 of interfacing surfaces 340 and 342.

In FIG. 2B, mating parts 302 and 303 are illustrated in a decoupled state, and the replacement scenario is assumed for the purposes of discussion. Connector 300 further includes a protection structure 341, e.g., a skirt or apron, projecting from interfacing surface 342 and configured to protect interfacing surfaces 340 and 342 against contaminant intrusion. Skirt 341 is formed on, e.g., outer area 346 of interfacing surface 342, and can be described as an extension of sidewalls 331.

Skirt 341 is configured to enclose inner areas 344 of interfacing surfaces 340 and 342. While mating parts 302 and 303 are decoupled, skirt 341 protects inner area 344 of interfacing surface 342, and thus the electrodes formed thereon, from contamination by body fluids that otherwise might wash over sidewalls 330 of mating part 303. Together, skirt 341 and inner area 344 of interfacing surface 342 define a recess in mating part 303. Mating part 302 is configured in the shape of a complementary projection sized to engage the recess.

Figure 2C:
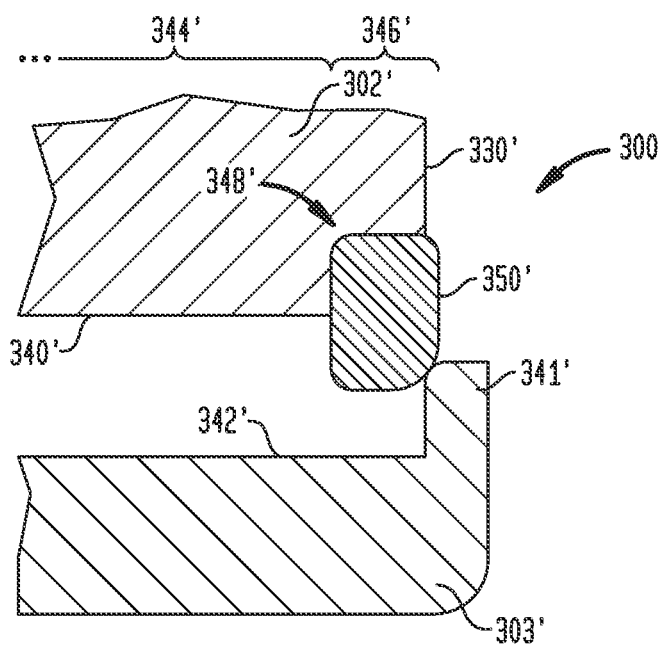
FIGS. 2C-2E are exploded partial cross-sections of another implantable connector 300' in which some embodiments of the present technology may be implemented.
Figure 2D:
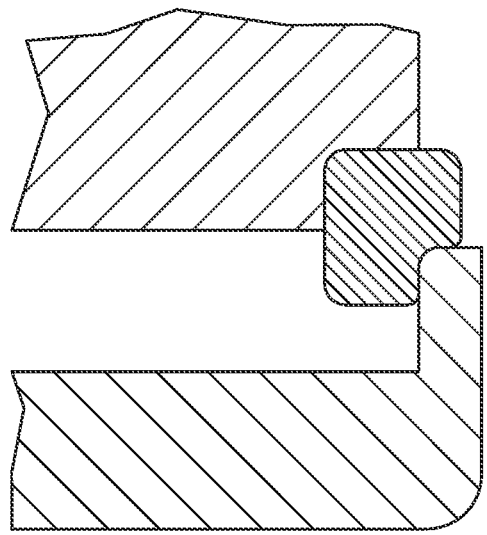
Figure 2E:
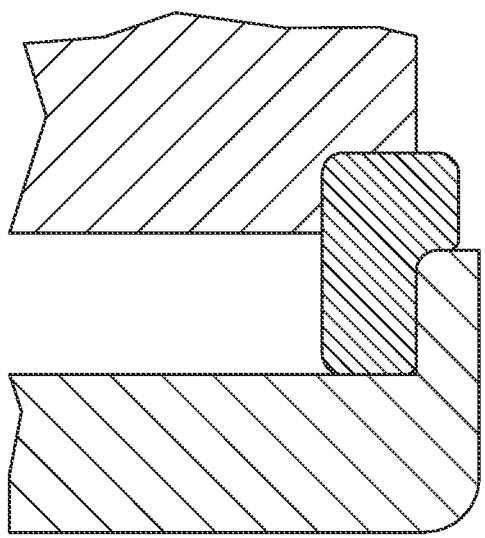

FIGS. 2C-2E are exploded partial cross-sections of another implantable connector 300' in which some embodiments of the present technology may be implemented. Connector 300' is similar in many respects to connector 300 of FIG. 2B, as indicated by similar numbering, and in some respects has been illustrated in less detail for the sake of brevity.

Mating part 302' is formed with a notch 348 between interfacing surface 340' and sidewall 330'. As such, for interfacing surface 340', inner area 344' stands proud of outer area 346' of interfacing surface 340'. In connector 300', the protection structure not includes skirt 341' but also includes a gasket 350', e.g., an o-ring. FIGS. 2A-2C illustrate mating part 302' being inserted progressively further into the recess formed by interfacing surface 342' and skirt 341', respectively. Gasket 350 can be formed of a resilient material, a foam material or a viscous material, that deforms upon compression.

FIG. 2F is a cross-section of another implantable connector 300'' in which some embodiments of the present technology may be implemented. Connector 300'' is similar in many respects to connector 300' of FIGS. 2C-2E, as indicated by similar numbering, and in some respects has been illustrated in less detail for the sake of brevity.

In particular, mating part 303'' is similar in many respects to mating part 103 of FIG. 1B, and mating part 302'' is similar in many respects to mating part 302' of FIGS. 2C-2E, as indicated by similar numbering, and in some respects has been illustrated in less detail for the sake of brevity. As contrasted with mating part 302', mating part 302'' has notches 348'' that are more inwardly formed (vis-à-vis sidewalls 330'') than are notches 348' (vis-à-vis sidewalls 330'). Gasket 350'' is similar to gasket 350'.

FIG. 2G is a cross-section, and FIG. 2H is a top view of one-half, of a mating part 403 of another implantable connector 400 in which some embodiments of the present technology may be implemented. Mating part 403 is similar in many respects to mating part 203 of FIG. 2A, as indicated by similar numbering, and in some respects has been illustrated in less detail for the sake of brevity.

Mating part 403 further includes a protection structure 452, e.g., a gutter, recessed into interfacing surface 442 and configured to protect interfacing surface 442 against contaminant intrusion. Gutter 452 is formed in, e.g., outer area 446 of interfacing surface 442, and is located inwardly of sidewalls 430. Gutter 452 is configured to enclose inner area 444 of interfacing surface 442. While mating part 403 is decoupled from its corresponding mating part (not illustrated), gutter 452 protects inner area 444 of interfacing surface 442, and thus electrodes 420 and 422, from contamination by body fluids that otherwise might wash over sidewalls 430 of mating part 403.

In FIG. 2H, mating part 403 is also illustrated with an optional groove 454 configured to extend from gutter 452 to sidewall 430 of mating part 403. Groove 454 facilitates draining of gutter 452, e.g., with assistance of a vacuum (negative pressure) from a surgical sucker 456.

Figures 3A, 3B, 3C, 3D:
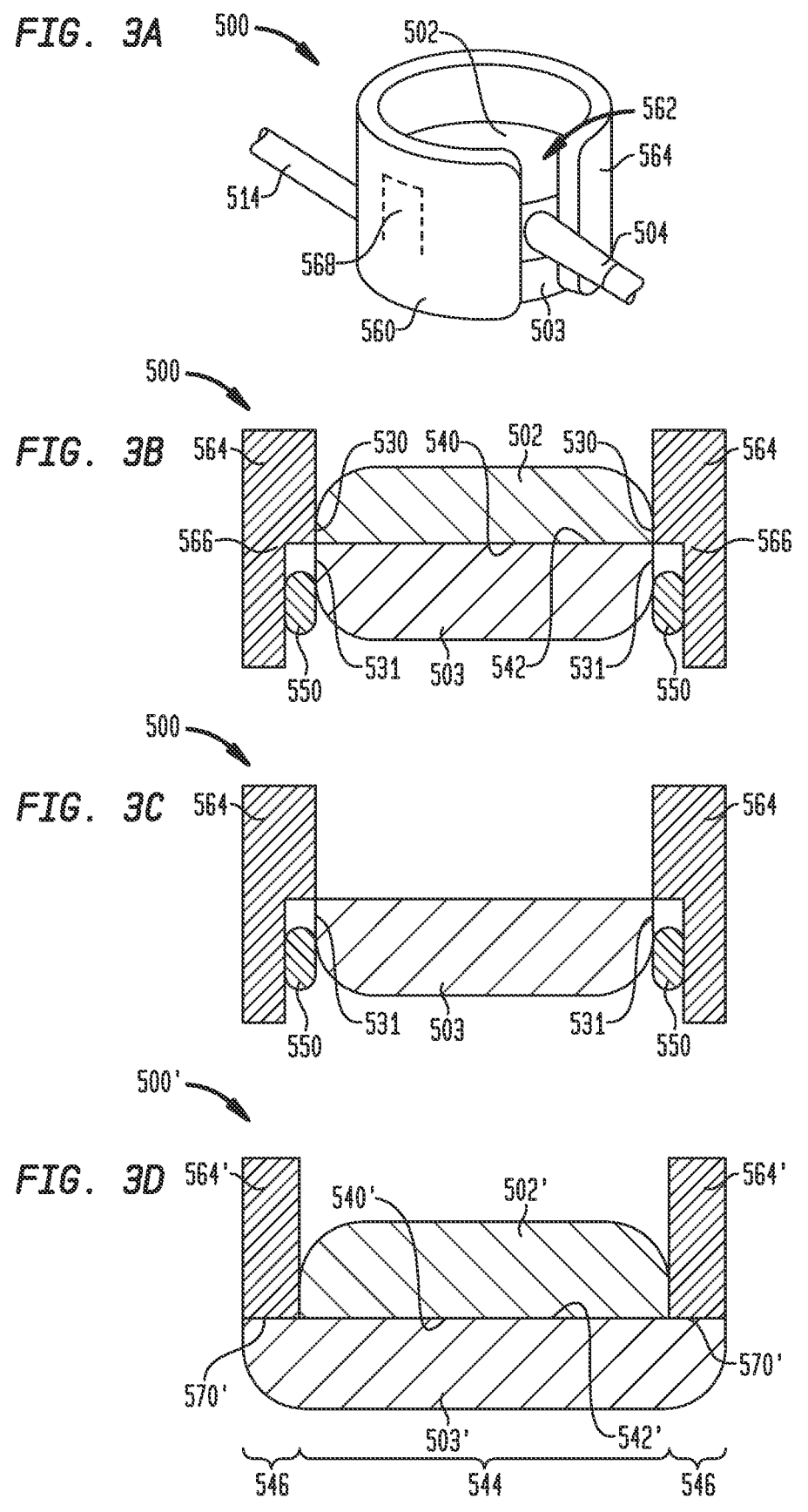

FIG. 3A is a three-quarter perspective view, and FIGS. 3B-3C are cross-sections, of a system 500, in which some embodiments of the present technology may be implemented, for protecting an implantable connector against contaminant intrusion between mating parts of the connector. The mating parts of the connector of system 500 can variously be similar in many respects to the mating parts, e.g., of FIGS. 2A and 2F-2G, as indicated by similar numbering, and in some respects have been illustrated in less detail for the sake of brevity.

In FIGS. 3A-3C, system 500 includes an implantable connector having first and second detachable mating parts 502 and 503 configured to be implantable in living tissue and terminate a first segment 504 and a second segment 514 of a cable, respectively. Mating parts 502 and 503 have interfacing surfaces 540 and 542 bounded by sidewalls 530 and 531, respectively. It is noted that FIG. 3C illustrates, e.g., a later stage in the context of the replacement scenario vis-à-vis FIG. 3B, wherein replace mating part 502 (illustrated in FIG. 3B but not in FIG. 3C) has been removed in preparation for subsequent re-coupling with a replacer mating part 502 (not illustrated). The various components of system 500 are formed of biocompatible materials, e.g., including one or more of Titanium, Silicone, Ceramic, Platinum, Platinum/Iridium, polyether ether ketone (PEEK), etc.

System 500 further includes a protection structure 560, e.g., a hollow cylinder, configured to enclose one or more of sidewalls 530 and 531. Cylinder 560 is formed with a slit 562 oriented substantially parallel to the axis of symmetry of cylinder 560. Slit 562 is configured to receive segment 504 of the cable. For example, one end of cylinder wall 564 can have formed therein a notch 568 configured to receive segment 514 of the cable. Notch 568 and slit 562 can be located on substantially opposite sides of cylinder 560. Wall 564 of cylinder 560 is further configured, e.g., to abuttingly enclose at least one or more of sidewalls 530 and 531.

Cylinder wall 564, e.g., has formed therein a notch 566 that can receive a gasket 550 that forms a seal between notch 566 and at least sidewall 531 of mating part 503. Alternatively, notch 556 could be located such that gasket 550 also forms a seal with sidewall 530 of mating part 502. Gasket 550 can be formed of a resilient material, a foam material or a viscous material, that deforms upon compression.

FIG. 3D is a cross-section of another system 500', in which some embodiments of the present technology may be implemented, for protecting an implantable connector against contaminant intrusion between mating parts of the connector. System 500' is similar in many respects to system 500 of FIGS. 3A-3C, as indicated by similar numbering, and in some respects has been illustrated in less detail for the sake of brevity.

Mating parts 502' and 503' of connector 500' have interfacing surfaces 540' and 542', respectively. Each of interfacing surfaces 540' and 542' is arranged with an inner area 544, e.g., a circular area. Interfacing surface 542' is further arranged with an outer area 546', e.g., an annular outer area, that encloses inner area 544'. Corresponding electrode pairs (not illustrated) are provided on inner areas 544' of interfacing surfaces 540' and 542'. As contrasted with mating part 503 (vis-à-vis mating part 502), mating part 503' is wider than mating part 502', the extra width corresponding to outer area 546' of interfacing surface 542'. Ends of sidewall 564' of cylinder 560 abut outer area 546' of interfacing surface 542'.

FIGS. 4A-4D are cross-sections that together illustrate another system 600 in which some embodiments of the present technology may be implemented, for protecting an implantable connector against contaminant intrusion between mating parts of the connector. The mating parts of the connector of system 600 can variously be similar in many respects to the mating parts, e.g., of FIGS. 2A-2H and 3A-3D, as indicated by similar numbering, and in some respects have been illustrated in less detail for the sake of brevity.

In FIGS. 4A-4C, system 600 includes an implantable connector having first and second detachable mating parts 602 and 603 configured to be implantable in living tissue and terminate first and second segments (not illustrated) of a cable, respectively. Mating parts 602 and 603 have interfacing surfaces 640 and 642 bounded by sidewalls 630 and 631, respectively. Corresponding electrode pairs (not illustrated) are provided on interfacing surfaces 640 and 642. FIGS. 4A-4C assume that mating part 603 is partially recessed in bone 126. The various components of system 600 are formed of biocompatible materials, e.g., including one or more of Titanium, Silicone, Ceramic, Platinum, Platinum/Iridium, polyether ether ketone (PEEK), etc.

System 600 further includes a protection structure 660, e.g., a coffer dam, configured to enclose sidewalls 631 of mating part 603. Coffer dam 660 can be spaced apart from sidewall 631 so as to leave a gap 670 therebetween. Alternatively, coffer dam 660 can be arranged to abut sidewall 631.

Whereas mating part 603 is relatively durable, coffer dam is, e.g., relatively transitory. For example, coffer dam 660 can be formed of a resilient, foam and/or viscous material. e.g., that is bioresorbable FIG. 4A is illustrated at a time at which mating parts 602 and 603 have been provided and coupled but before coffer dam 660 has been provided. FIG. 4B is illustrated at a time that coffer dam 660 is partially formed. In FIG. 4B, a nozzle 672 is illustrated as providing source material for coffer dam 660. An operator can move nozzle 672 circumferentially around sidewall 631 as the material is being dispensed, thereby forming coffer dam 660.

FIG. 4C is illustrated at a time after coffer dam 660 has been provided to system 600, and further illustrates alternatively three stages in a procedure to replace an instance of mating part 602 (the "replacee" version of mating part 602) by another instance of mating part 602 (the "replacer" version of mating part 602) while mating part 603 remains in its implanted position. A first stage illustrated by FIG. 4C is denoted by arrow 674, and represents the "replacee" version of mating part 602 being decoupled from mating part 603. A second stage illustrated by FIG. 4C is denoted by arrow 676, and represents the "replacer" version of mating part 602 being re-coupled to mating part 603. A third stage illustrated by, FIG. 4C can be understood as illustrated at a time when mating parts 602 and 603 are in decoupled state before they are initially coupled (the initially coupling being noted by arrow 676). When mating part 602 is decoupled from mating part 603, a surface 642 of mating part 603 (on which the electrodes (not illustrated) are located) is placed at risk of contamination by body fluids that would otherwise wash over sidewalls 631 of mating part 603 if coffer dam 660 were not provided.

FIGS. 5A-5B are cross-sections of another system 700 in which some embodiments of the present technology may be implemented, for protecting a mating part 705 of an implantable connector against contaminant intrusion. Mating part 705 can variously be similar in many respects to mating parts, e.g., 102 and 103 of FIGS. of 1A-1D, 202 ad 203 of FIG. 2A, 302 and 303 of FIG. 2B, 302' and 303' of FIGS. 2C-2E, 302" and 303" of FIG. 2F, 403 of FIGS. 2G-2H, 502 and 503 of FIGS. 3A-3C, 502' and 503' of FIG. 3D, and 602 and 603 of FIGS. 3A-3D, as indicated by similar numbering, and in some respects has been illustrated in less detail for the sake of brevity.

In FIGS. 5A-5B, mating part 705 is configured to be implantable in living tissue and terminate a segment (not illustrated) of a cable. Mating part 705 has an interfacing surface 747 bounded by sidewall 733. Electrodes (not illustrated) are provided on interfacing surface 747 in correspondence to electrodes (not illustrated), respectively, on a corresponding mating part (not illustrated). Mating part 705 is formed of biocompatible materials, e.g., including one or more of Titanium, Silicone, Ceramic, Platinum, Platinum/ Iridium, polyether ether ketone (PEEK), etc.

System 700 not only includes mating part 705, but also a protection structure 778 configured to protect interfacing surface 474 against contamination. For example, protection structure 778 includes a removable layer 778, e.g., a protective film, disposed in contact with interfacing surface 747 so as to seal the same from the ambient environment. Removable layer 778 temporarily adheres to interfacing surface 747, protecting it from contamination until mating part 705 is ready for coupling to a counterpart mating part, at which time the person intending to couple the mating parts, e.g., a surgeon, may remove layer 778. Optionally, layer 778 can include one or more portions that overhang one or more edges of sidewall 733 and thus serve as one or more tabs 779, each of which can be grasped and thereby used to exert a force on layer 778 by which to remove layer 778.

FIGS. 6A-6C are cross-sections of another connector 800 in which some embodiments of the present technology may be implemented. The mating parts of connector 800 can variously be similar in many respects to the mating parts, e.g., of FIGS. 1A-1D, 2A-H, 3A-D, etc., as indicated by similar numbering, and in some respects have been illustrated in less detail for the sake of brevity.

In FIGS. 6A-6B, mating parts 802 and 803 are configured to be implantable in living tissue, e.g., mating part 803 is configured to be partially recessed in bone 126, and terminate first and second segments (not illustrated) of a cable, respectively. Mating parts 802 and 803 have interfacing surfaces 840 and 842 bounded by sidewalls 830 and 831, respectively. Corresponding electrode pairs (not illustrated) are provided on interfacing surfaces 840 and 842. Connector 800 is formed of biocompatible materials, e.g., including one or more of Titanium, Silicone, Ceramic, Platinum, Platinum/Iridium, polyether ether ketone (PEEK), etc.

Mating part 803 includes at least one alignment projection 880 extending substantially perpendicularly from interfacing surface 842. Mating part 802 includes at least one alignment hole corresponding to the at least one alignment projection 880, respectively, each alignment hole 882 being complementarily shaped to receive corresponding alignment projection 880. The at least one alignment projection 880 also is formed of biocompatible materials, e.g., including one or more of Titanium, Silicone, Ceramic, Platinum, Platinum/ Iridium, polyether ether ketone (PEEK), etc.

Recesses 882 are formed in alignment with associated projections 880 so insertion of alignment projections 880 into recesses 882 causes mating parts 802 and 803 to align, thereby facilitating a good electrical connections between electrodes of corresponding pairs thereof (not illustrated) provided on interfacing surfaces 840 and 842.

Optionally, each alignment hole 882 can extend through mating part 802 to form a through-hole in one or more opposing second surfaces 886 thereof. Each alignment projection 880 can include a portion 884 that stands proud of surface(s) 886 of mating part 802. Also, optionally, one or more proud-standing portions 884 can be configured as a flange 888. Each flange 888 and the corresponding hole 882 have a diameter extending in a direction substantially perpendicular to the long axis of the alignment projection, with flange 888 being wider than hole 882. Flange 888 resists mating part 802 from a tendency (if any) to decouple from mating part 803.

FIG. 7A is a top view, and FIG. 7B is a cross-section, of a machine 900, in which some embodiments of the present technology may be implemented, for manipulating mating parts of an implantable connector. The mating parts of the connector that are manipulable by machine 900 can variously be similar in many respects to the mating parts, e.g., of FIGS. 1A-1D, 2A-H, 3A-D, 6A-6C, etc., as indicated by similar numbering, and in some respects have been illustrated in less detail for the sake of brevity.

In FIGS. 7A-7B, a first mating part 903 and first and second instances 902A and 902B of a second mating part are configured to be implantable in living tissue, e.g., mating part 903 being partially recessed in bone 126, and terminate a first segment (not illustrated) and first and second instances 904A and 904B of a second segment of a cable, respectively. Instances 904A and 904B of second segment of a cable are connected to first and second instances 990A and 990B of another component.

First and second instances 902A and 902B of the second mating part 902A and mating part 903 have first and second instances 940A and 940B of a second interfacing surface and a first interfacing surface 942 bounded by first and second instances 930A and 930B of a sidewall and a sidewall 931, respectively. Corresponding electrode pairs (not illustrated) are provided on first and second instances 940A and 940B of the second interfacing surface and on interfacing surface 942. The connector comprising mating parts 902A and 903 is formed of biocompatible materials, e.g., including one or more of Titanium, Silicone, Ceramic, Platinum, Platinum/Iridium, polyether ether ketone (PEEK), etc.

Machine 900 includes an enclosure 992 and a coupling device 996. Enclosure 992 is configured to releasably enclose at least first and second instances of mating part 902A and 902B and a portion of mating part 903 in an environmentally controllable volume 994, e.g., a hermetically sealable volume. Enclosure 992 can be a multi-piece assembly. Coupling device 996 is configured to at least one of decouple and re-couple mating part 903 and instances 902A and 902B of the second mating part, respectively, while instances 902A and 902B of the mating part and the portion of mating part 903 are disposed in environmentally controllable volume 994.

During operation of machine 900, mating part 903 is stationary relative to instances of mating part 902A and 902B. Coupling device 996 includes: a decoupling apparatus 998 and a re-coupling apparatus 1000. Decoupling apparatus 998 is configured to: decouple mating part 903 and instance 902A of the second mating part; and move instance 902A of the second mating part along an arcuate path 1002 away from mating part 903. Re-coupling apparatus 1000 is configured to: move instance 902B of the second mating part along arcuate path 1002 towards mating part 903; and re-couple first mating part 903 to second instance 902B of the second mating part. Coupling device 996 also can include, e.g., a cleaning apparatus 1002 configured to clean mating part 903 and instance 902A of the second mating part. Cleaning apparatus 1002 can include: an irrigation apparatus 1004 to wash mating part 903 and instance 902A of the second mating part; and a drying apparatus 1006 to dry mating part 903 and instance 902A of the second mating part.

In FIGS. 7A-7B, there is a rotational axis 1008 about which the motion along arcuate path 1002 occurs. Decoupling and re-coupling is associated with motion along a coupling axis 1010, where coupling axis 1010 is substantially parallel to but radially displaced from rotational axis 1008. Machine 900 further includes a crankshaft 1012 that is coaxial with rotational axis 1008. Coupling device 996 is mounted to crankshaft 1012. More particularly decoupling apparatus 998, irrigation apparatus 1004, drying apparatus 1006 and re-coupling apparatus 1000 are mounted to crankshaft 1012, via mechanisms 1014-1017, respectively. Inducing rotation of crankshaft 1012 can cause instances 902A and 902B of the second mating part to be moved along arcuate path 1002 away from mating part 903. Gaskets 1014 and 1016 make a seal between crankshaft 1012 and enclosure 992. Gasket 1018 makes a seal between mating part 903 and enclosure 992.

FIG. 7C is a cross-section of another machine 900', in which some embodiments of the present technology may be implemented, for manipulating mating parts of an implantable connector. Machine 900' is similar in many respects to machine 900 of FIGS. 7A-7B, as indicated by similar numbering, and in some respects has been illustrated in less detail for the sake of brevity.

In FIG. 7C, there is a rotational axis 1008' about which the motion along arcuate path 1002' occurs. Decoupling and re-coupling is associated with motion along a coupling axis 1010', where coupling axis 1010' is substantially orthogonal to rotational axis 1008'.

The present technology described and claimed herein is not to be limited in scope by the specific example embodiments herein disclosed, since these embodiments are intended as illustrations, and not limitations, of several aspects of the present technology. Any equivalent embodiments are intended to be within the scope of the present technology. Indeed, various modifications of the present technology in addition to those shown and described herein will become apparent to those skilled in the art from the foregoing description. Such modifications are also intended to fall within the scope of the appended claims.

What is claimed is:

1. An implantable connector comprising:
    a first mating part comprising a first interfacing surface and a first terminating segment of a communication cable; and
    a second mating part comprising a second interfacing surface and a second terminating segment of the communication cable, wherein each of the first mating part and the second mating part are configured:
        to be implantable in living tissue; and
        to detachably mate at the first and the second interfacing surfaces;
    and
    a protection structure configured to protect against contaminant intrusion between the first and second interfacing surfaces.

2. The connector of claim 1, wherein:
    each of the first and second interfacing surfaces has an inner area and at least one of the first and second interfacing surfaces has an outer area enclosing the inner area;
    the first and second segments of the communication cable are connected to at least a first pair of contacts provided on the inner areas of the first and second interfacing surfaces, respectively; and
    the protection structure is positioned in the outer area and is further configured to enclose the inner areas of the first and second interfacing surfaces, respectively.

3. The connector of claim 1, wherein:
the protection structure includes at least one of:
- a gasket;
- a wall projecting from one of the first and second interfacing surfaces; and
- a gutter formed in one of the first and second interfacing surfaces.

4. The connector of claim 3, wherein:
the protection structure includes the wall;
the wall projects from the first interfacing surface such that the wall and the first interfacing surface define a recess in the first mating part; and
the second interfacing surface of the second mating part is configured in a shape of a complementary projection sized to engage the recess.

5. The connector of claim 4, wherein:
the protection structure also includes the gasket; and
the gasket is disposed between the projection and the wall.

6. The connector of claim 4, wherein:
an inner area stands proud of an outer area of the first interfacing surface; and
the gasket is disposed in a notch formed by the inner and outer areas of the first interfacing surface; and
the gasket stands proud of the inner area of the first interfacing surface.

7. The connector of claim 3, wherein:
the gasket is an o-ring.

8. The connector of claim 3, wherein:
the gutter is formed in the first interfacing surface;
the first mating part has a sidewall intersecting the first interfacing surface; and
the protection structure further includes:
- a groove configured to extend from the gutter to the sidewall of the first mating part and thereby facilitate draining of the gutter.

9. The implantable connector of claim 1, wherein the protection structure is retained in a notch defined by at least one of the first mating part and the second mating part.

10. The implantable connector of claim 1, wherein the protection structure comprises a skirt projecting from at least one of the first mating part and the second mating part.

11. The implantable connector of claim 1, wherein the protection structure comprises a deformable element.

12. A system for protecting an implantable connector having a first detachable mating part configured to be implantable in living tissue and terminate a first segment of a communication cable, and a second detachable mating part configured to be implanted in living tissue and terminate a second segment of the communication cable, each mating part having an interfacing surface bounded by one or more sidewalls, the system comprising:
a protection structure configured to enclose the one or more sidewalls of at least one of the first and second mating parts.

13. The connector of claim 12, wherein:
the protection structure includes a hollow cylinder comprising a
cylinder wall having formed therein a slit oriented substantially parallel to the axis of symmetry of the hollow cylinder and being configured to receive the second segment of the communication cable; and
the cylinder wall is further configured to abuttingly enclose at least the one or more sidewalls of the second mating part.

14. The connector of claim 13, wherein:
each of the interfacing surfaces has an inner area and the interfacing surface of the first mating part also has an outer area enclosing the inner area; and
an end the cylinder wall abuts the outer area of the first interfacing surface.

15. The connector of claim 13, wherein:
the protection structure further includes at least one gasket disposed between the cylinder wall and the one or more sidewalls of at least one of the first and second mating parts.

16. The connector of claim 13, wherein:
the cylinder wall has formed at one end thereof a notch configured to receive the first segment of the communication cable.

17. The connector of claim 12, wherein:
the first mating part is configured so as to be recessed in the tissue; and
the protection structure includes a coffer dam disposed on the tissue and configured to enclose at least the one or more sidewalls of the second mating part.

18. The connector of claim 17, where:
the first mating part is relatively durable; and
the coffer dam is relatively transitory.

19. The connector of claim 18, wherein:
the coffer dam includes at least one of:
- a viscous material; and
- a foam material.

20. The connector of claim 12, wherein:
the connector is a button type of connector.

21. The system of claim 12, wherein the protection structure is retained in a notch defined by at least one of the first mating part and the second mating part.

22. The system of claim 12, wherein the protection structure comprises a skirt projecting from at least one of the first mating part and the second mating part.

23. The system of claim 12, wherein the protection structure comprises a deformable element.

* * * * *